(12) United States Patent
Subramanyam

(10) Patent No.: US 8,425,881 B2
(45) Date of Patent: *Apr. 23, 2013

(54) ANTIBACTERIAL 3',5-DISUBSTITUTED 2,4'-DIHYDROXYBIPHENYL COMPOUNDS, DERIVATIVES AND RELATED METHODS

(75) Inventor: Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 724 days.

This patent is subject to a terminal disclaimer.

(21) Appl. No.: 11/369,430

(22) Filed: Mar. 7, 2006

(65) Prior Publication Data
US 2006/0210489 A1 Sep. 21, 2006

Related U.S. Application Data

(60) Provisional application No. 60/662,991, filed on Mar. 18, 2005.

(51) Int. Cl.
*A61K 8/00* (2006.01)

(52) U.S. Cl.
USPC ........................................... 424/49

(58) Field of Classification Search ............ 424/49
See application file for complete search history.

(56) References Cited

U.S. PATENT DOCUMENTS

| | | | |
|---|---|---|---|
| 3,429,963 A | 2/1969 | Shedlovsky | |
| 5,292,526 A | 3/1994 | Gaffar et al. | |
| 5,356,615 A * | 10/1994 | Gaffar | 424/49 |
| 5,472,684 A | 12/1995 | Nabi et al. | |
| 6,342,205 B1 | 1/2002 | Niemi et al. | |
| 6,379,652 B1 | 4/2002 | Liu et al. | |
| 6,511,966 B2 | 1/2003 | Ghosh et al. | |
| 6,740,311 B2 | 5/2004 | White, Jr. et al. | |
| 6,977,082 B2 | 12/2005 | Seitz, Jr. et al. | |
| 7,196,117 B2 | 3/2007 | Beltran et al. | |
| 7,205,266 B2 | 4/2007 | Holderbaum et al. | |
| 2003/0049303 A1 * | 3/2003 | Ning et al. | 424/439 |
| 2006/0120975 A1 | 6/2006 | Scherl et al. | |
| 2006/0140880 A1 * | 6/2006 | Subramanyam et al. | 424/49 |
| 2006/0141072 A1 | 6/2006 | Arvanitidou et al. | |
| 2006/0233722 A1 | 10/2006 | Subramanyam | |

FOREIGN PATENT DOCUMENTS

| | | |
|---|---|---|
| EP | 0850912 | 7/1998 |
| EP | 1405851 | 4/2004 |
| JP | 07033649 | 2/1995 |
| JP | 9176074 | 7/1997 |
| JP | 9278638 | 10/1997 |
| JP | 2000-169846 A | 6/2000 |
| JP | 2004292392 | 10/2004 |
| KR | 20020004025 | 1/2002 |
| WO | WO 97/10800 | 3/1997 |
| WO | WO 01/82922 | 11/2001 |
| WO | WO 01/85116 | 11/2001 |
| WO | WO 2006/060145 | 6/2006 |

OTHER PUBLICATIONS

Namba et al. "Studies on dental caries prevention by traditional Chinese medicines, Screening of crude drugs for inhibitory action on plaque formation". Accession No. 1983:609662. Chemical Abstracts Services. 1982.*

Fujisawa, S. et al. "Application of *bis* -eugenol to a zinc oxide eugenol cement". Journal of Dentistry 27. (1999). pp. 291-295.

Namba, Tsuneo et al. "Studies on dental caries prevention by traditional Chinese medicines. Screening of crude drugs for inhibitory action on plaque formation". Accession No. 1983:609662, Chemical Abstracts Service. 1982.

Asano et al., 1949, Database Beilstein Registry Nos. 3379472, 3424700, 2620747, J. Am. Pharm. Assoc. 38:169-172.

Baehni et al., 2003, "Anti-Plaque Agents in the Prevention of Biofilm-Associated Oral Diseases," Oral Diseases 9:23-29.

Botelho, 2000, "Fractional Inhibitory Concentration Index of Combinations of Antibacterial Agents Against Cariogenic Organisms," J. of Dentistry 28:565-570.

Chiang et al., 1952, Database Beilstein Registry No. 3352973, J. Am. Pharm. Assoc. 41:348-349.

Delogu et al., 2004, "Enantiopure 2,2-dihydroxy 3,3'-dimethoxy-5-5' dially1-6,6'-dibromo-1,1'- biphenyl: A Conformationally Stable $C_2$-Dimer of a Eugenol Derivative," Tetrahedron: Asymmetry 15(2):275-282 (pp. 275-276 submitted).

Eistert et al., 1962, "Reactions of Diazoacetic Ester and Diazo-Acetophenone with Di- and Triphenyl-Cyclopentene-Diones," Justus Liebigs Annalen der Chemie 657:120-131.

Evans et al., 1984, "Identification of Fungicidal and Nemalocidal Components in the Leaves of the Piper betle (Piperaceae)," J. Agricultural Food Chem. 32:1254-1256.

Furiga et al., 2008, "In vitro Anti-Bacterial and Anti-Adherence Effects of Natural Polyphenoloic Compounds on Oral Bacteria," J. Applied Microbiology 105:1470-1476.

(Continued)

*Primary Examiner* — Jeffrey S. Lundgren
*Assistant Examiner* — Chris Simmons
(74) *Attorney, Agent, or Firm* — Howard C. Lee

(57) ABSTRACT

The invention provides an antiplaque oral composition containing an orally acceptable carrier and an antibacterial effective amount of compound (I):

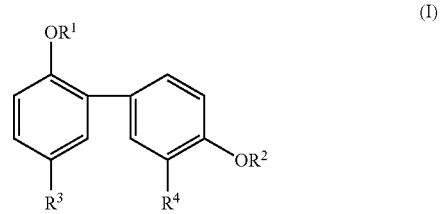

(I)

In the structure, $R^1$ and $R^2$ are independently a hydrogen atom or a lower $C_{1-4}$ alkyl group and $R^3$ and $R^4$ are independently an alkenyl or alkyl group having from 1 to 20 carbon atoms, with the proviso that $R^3$ and $R^4$ are not both 2-propenyl or n-propyl when $R^1$ and $R^2$ are both hydrogen atoms. Also included are oral compositions containing the compound (I).

25 Claims, 1 Drawing Sheet

OTHER PUBLICATIONS

Ito et al., 2004, "Preparation of Dialyklbisphenols by Oxidative Coupling of p-Alkylphenols," Chemical Abstracts Service STN Database Accession No. 2004:873842.

International Search Report and Written Opinion in International Application No. PCT/US08/078096, mailed Jan. 26, 2009.

Kobayashi et al., 1997, "Eugenol Isoeugenol Dimers as Bactericides, Fungicides, and Inflammation Inhibitors," Chemical Abstracts Services JP 09176074 Accession No. 1997:580683.

Kong et al., 2005, "Cytotoxinc Neolignans: an SAR Study," Bioorganic & Medicinal Chemistry Letters 15:163-166.

Liberato et al., 1981, "Regiospecific attack of nitrogen and sulfur nucleophiles on quinones derived from poison oak/ivy catechols (urushiols) and analogues as models for urushiol-protein conjugate formation," J. Med. Chem. 24(1):28-33.

Marsh, 2003, "Plaque as a Biofilm: Pharmacological Princibles of Drug Delivery and Action in the Sub- and Supragingival Environment," Oral Diseases 9:16-22.

Maruyama et al., 1981, "A Convenient Allylation of Ortho-Quinones. An Extension on the Utility of Allyltin Reagents," Chemistry Letters 10:47-50.

Mergenhagen et al., 1970, "Immunologic Reactions and Periodontal Inflammation," J. Dental Research 49:256-261.

Merriam Webster's Definition for Lozenge, http://wwvv.merriam-webster.com/dictionary/lozenge.

Murakami et al., 2003, "Preventive Effect of bis-Eugenol, a Eugenol Ortho Dimer, on Lipopolysaccharide-Stimulated Nuclear Factor Kappa B Activation and Inflammatory Cytokine Expression in Macrophages," Biochemical Pharmacology 66:1061-1066.

Ogata et al., 1997, "Antioxidant Activity of Magnolol, Honikiol, and Related Phenolic Compounds," JAOCS 74(5):557-562.

Omote et al., 1976, Database Beilstein Registry No. 2161803, Chemistry and Industry p. 904.

Ramji et al., 2002, "Phenolic Antibacterials from Piper betle in the Prevention of Halitosis," J. Ethnopharmacol. 83:149-152.

Sethi et al., 1964, "Synthesis of 4-Allylcatechol and Mechanism of Claisen Rearrangement in o-Dihydroxy Compounds," Indian J. Chem. 2:323-326.

Silverman, 1992, The Organic Chemistry of Drug Design and Drug Action, London, Academic Press, Inc., pp. 15-22.

J.M. ten Cate et al., 1994, "Procedures for Establishing Efficacy of Antimicrobial Agents for Chemotherapeutic Caries Prevention," J. Dental Research 73(3):695-703.

Zhang, 1999, "Theoretical Methods Used in Elucidating Activity Differences of Phenolic Antioxidants," JAOCS 76(6):745-748.

* cited by examiner

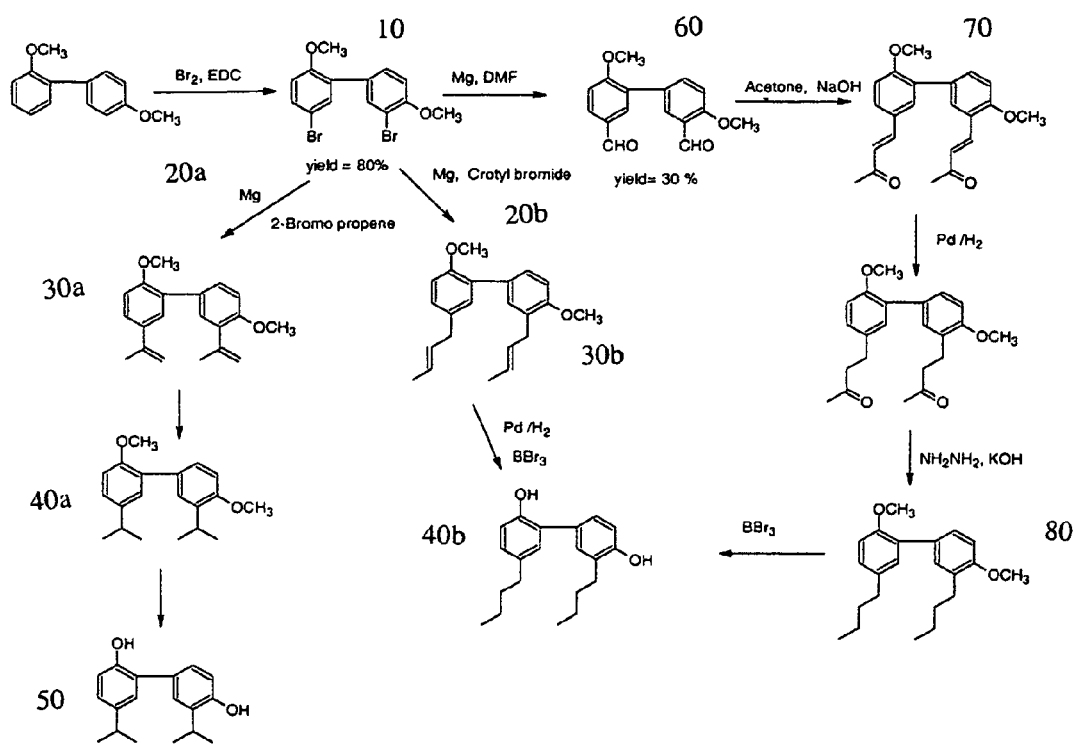

ANTIBACTERIAL 3',5-DISUBSTITUTED 2,4'-DIHYDROXYBIPHENYL COMPOUNDS, DERIVATIVES AND RELATED METHODS

CROSS REFERENCE TO RELATED APPLICATION

This application claims priority to U.S. Provisional Patent Application No. 60/662,991, filed Mar. 18, 2005, the contents of which are incorporated herein by reference.

BACKGROUND OF THE INVENTION

A number of disease conditions are associated with the action of bacteria in the oral cavity. Dental plaque is a soft deposit that forms on the surface of the teeth as a by-product of bacterial growth. Gingivitis, an inflammation or infection of the gums and alveolar bones, is generally believed to be caused by plaque causing bacteria and the toxins formed as by-products from the bacteria. In addition, plaque provides a locus for calculus or tartar formation. Periodontitis is generally believed to occur where unremoved plaque hardens into calculus (tartar), which effects the periodontal ligaments. As plaque and tartar continue to build up, the gums begin to recede, which can lead to continued infection and potentially the loss of teeth.

To prevent or treat these diseased conditions, antibacterial agents are incorporated into oral care compositions such as toothpaste and mouthwashes or rinses. Application of antibacterial compositions in the oral cavity tends to retard plaque formation and related oral infections.

The antiplaque efficacy of antibacterial compounds in a dentifrice composition depends on a number of factors, including the presence of other ingredients that may interfere with its action. For example, certain cationic antibacterial compounds and certain nonionic antibacterial compounds lose their effectiveness when formulated with certain anionic surfactants or other anionic active ingredients, such as tartar control phosphates. In many instances, it is preferred to use antibacterial compounds that do not show the adverse interactions with such anionic components.

Extracts from *Magnolia officinalis* (hereinafter "*magnolia*"), and especially from the bark, contain biphenol antibacterial compounds that include honokiol and tetrahydrohonokiol. The extracts have been found to have antibacterial effectiveness when formulated into, for example, toothpaste formulations.

Extracts prepared from natural sources such as *magnolia* are variable in composition and contain many compounds other than the particular actives for which the extract is prepared. The mode of activity of the extract compounds is not well characterized, so that it is unpredictable how alterations in structure of any of the extract compounds would affect its antibacterial effectiveness. In addition, the composition of the extracts can vary from season to season and between different geographical regions. As a result, the antibacterial activity of the extracts in vivo is far from optimal.

DESCRIPTION OF THE INVENTION

A class of 3',5-disubstituted 2,4'-dihydroxy- and -dialkoxy-1,1'-biphenyl compounds exhibits inhibitory action against a variety of bacteria commonly found in the oral cavity. The compounds are used as antiplaque and/or antibacterial components of dentifrices and other oral compositions. The invention provides various oral compositions containing the compounds and an orally acceptable carrier. In various embodiments, antibacterial and antiplaque oral compositions are provided in the form of a toothpaste or gel, a tooth powder, a mouthwash or mouth rinse, a lozenge, chewing gum, an edible strip, and the like. The antibacterial compounds are conveniently synthesized using conventional coupling, alkylation, reduction, and demethylation steps, although any means of synthesis known or developed in the art can be used.

The invention provides disubstituted 2,4'-diphenols and derivatives represented by the structure:

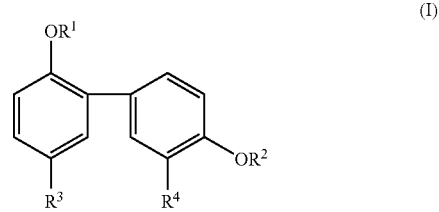

(I)

and exclusive of honokiol and tetrahydrohonokiol. $R^1$ and $R^2$ are independently H or a lower $C_{1-4}$ alkyl group and $R^3$ and $R^4$ are independently an alkenyl or alkyl group having from 1 to 20 carbon atoms, with the proviso that $R^3$ and $R^4$ are not both 2-propenyl or n-propyl when $R^1$ and $R^2$ are both H. Preferably, R contains 1 to 8 carbon atoms.

Antiplaque oral compositions are provided that contain an orally acceptable carrier and an antibacterial effective amount of at least one compound of structure (I). In various embodiments, the compositions contain from about 0.001% to about 10% by weight of (I). Without limitation, the orally acceptable carrier may be a liquid carrier; a powder carrier; or a carrier that dissolves upon contact with saliva and other components of an oral environment. In other embodiments, the carrier can comprise a gum base. The oral compositions are provided variously in the form of a toothpaste or gel, a tooth powder, a mouth rinse, a lozenge, chewing gum, and an edible strip. Other forms of the composition include without limitation a liquid suitable for painting a dental surface, a wafer, a wipe or towelette, an implant, a dental floss, and forms that are edible or chewable by smaller mammals, such as dogs or cats.

In other embodiments, the invention provides toothpaste or gel compositions that contain at least one humectant, at least one abrasive material, and an antibacterial effective amount of at least one compound of structure (I). In various embodiments, the toothpaste or gel compositions further comprise an anticalculus agent such as a phosphate compound, alternatively combined with synthetic anionic polycarboxylates. In an exemplary embodiment, the toothpaste or gel composition comprises 0.001-5% by weight of compound (I);
1-70% by weight humectant;
1-70% by weight abrasive compounds;
0.5-2.5% by weight tetrasodium pyrophosphate (TSPP); and
1-10% by weight sodium tripolyphosphate (STPP).

In other embodiments, the invention provides a method for inhibiting bacterial growth in the oral cavity of a subject animal, human or non-human, comprising applying to the oral surfaces of the subject animal an antibacterial composition comprising at least one compound of structure (I). In various embodiments, the method involves brushing the teeth and rinsing with compositions containing compound (I). As above, the method can be practiced by applying the antibacterial composition in a wide variety of forms such as toothpastes, tooth gels, tooth powder, mouth rinse, paint on gels, dissolvable or edible strips, chewing gum, lozenges, and the like. In various embodiments, treatment of oral surfaces with antibacterial compositions containing compound (I) leads to reduction or elimination of plaque, to prevention or treatment of gingivitis, to amelioration of oral malodor, and prevention of periodontal disease.

In various embodiments, the antibacterial compounds are selected from a class of 3',5-disubstituted-2,4'-dihydroxy-1,1'-biphenyls, represented by the structure:

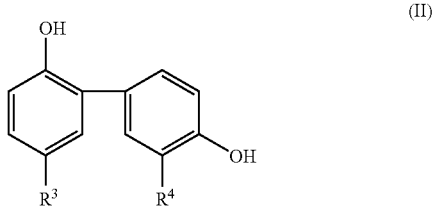

(II)

where $R^3$ and $R^4$ independently represent an alkenyl or alkyl group of 1 to 20 carbon atoms, with the proviso that $R^3$ and $R^4$ are not simultaneously 2-propenyl or n-propyl. Structure (II) corresponds to structure (I) where $R^1$ and $R^2$ are both hydrogen.

In some embodiments of structures (I) and (II), both $R^3$ and $R^4$ are alkyl groups. In other embodiments, both $R^3$ and $R^4$ are alkenyl groups. In yet other embodiments, one of the groups $R^3$ and $R^4$ is an alkyl group and the other is an alkenyl group. In various embodiments, the groups $R^3$ and $R^4$ are the same. In various embodiments, oral compositions containing compounds (I) and/or (II) exhibit antibacterial efficacy comparable to compositions containing triclosan.

The size and nature of the alkyl or alkenyl groups $R^3$ and $R^4$ are selected to achieve a desired combination of solubility and bioavailability in the compounds of structures (I) and (II). The compounds of structure (I) and (II) tend to be lipid soluble; distribution of the compounds between a lipid and water phase is reflected in a value of log P well known to those of skill in the art. In various embodiments, a log P value of 3 to 5 is preferred. In general, the larger the groups $R^3$ and $R^4$ (i.e., the higher the number of carbon atoms in the alkyl or alkenyl groups), the higher the solubility in lipid and the lower the solubility in water. The size of the groups $R^3$ and $R^4$ also affects the molecular weight and thus the molar amount of compounds (I) or (II) delivered by a unit dose. In a preferred embodiment, the groups $R^3$ and $R^4$ are selected such that the solubility of the compound (I)n water is 1 ppm or greater, preferably 5 ppm or greater, and more preferably 10 ppm or greater.

The compounds described herein may be synthesized via any means known or to be developed in the art. An exemplary synthesis of compounds (I) and (II) for the embodiment where $R^1$ and $R^2$ are either H or methyl is illustrated in the following scheme

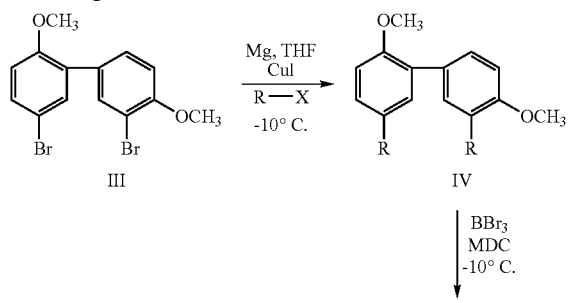

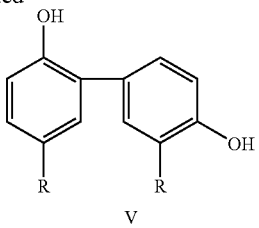

V

A dibromo intermediate (III) is alkylated to a dimethyl intermediate (IV), which is demethylated to arrive at compounds (V). Compounds (IV) and (V) of the reaction scheme correspond to embodiments of structure (I) and (II), respectively, of the invention. The dibromo intermediate can be alkylated, for example, under conventional Grignard reaction conditions as shown. R—X represents an alkyl or alkenyl halide, with R as defined above for $R^3$ and $R^4$ and X representing a halogen, preferably bromine. When a single halide is used in the Grignard reaction, an embodiment of compounds (I) and (II) is synthesized wherein $R^3$ and $R^4$ are the same. If desired, a mixture of halides can be used to prepare embodiments of compounds (I) and (II) wherein $R^3$ and $R^4$ are different. In various embodiments complete or partial dealkylation (shown as complete demethylation) of the resulting structure (IV) proceeds according to known procedures, illustrated in the scheme by stirring with boron tribromide in dimethylene chloride at −10° C. Starting materials (III) can be readily synthesized. In a non-limiting example, p-iodoanisole is coupled to 2-methoxyphenylboronic acid to give an intermediate that is brominated to form (III). In an exemplary embodiment, the coupling reaction is carried out in the presence of palladium tetraphenyl phosphate, potassium carbonate and a phase transfer catalyst such as tetrabutyl ammonium bromide. Bromination of the coupling reaction product proceeds readily, for example at 0° C. in $Br_2$ and ethylene dichloride.

Other non-limiting synthetic routes to alkyl and alkenyl compounds of structures (I) and (II) are given in FIG. 1. In one alternative synthetic pathway, a dibromo intermediate 10 is reacted with an alkenyl bromide (illustrated in the alternative embodiments of 2-bromopropene 20a and crotyl bromide 20b) to make alkenyl compounds 30a and 30b where $R^1$ and $R^2$ are methyl. As shown, the alkenyl compounds 30a and 30b can be reduced to form corresponding alkyl compounds 40a and 40b, with optional subsequent dealkylation (illustrated as a demethylation) to a diol 50. In another pathway, the dibromo intermediate 10 is converted to a dialdehyde intermediate 60, followed by Claissen-type condensation with a ketone (exemplified by acetone) to form another intermediate 70 with a 4 carbon chain. Other ketones can be used to provided chains longer than 4. The double bond and the oxo group of the intermediate side chain are then reduced to form compound 80 with a saturated alkyl chain for $R^3$ and $R^4$. The alkyl groups (illustrated as methyl groups) can be removed to form the 2,4'-dihdroxy compounds 40b.

The antibacterial compound of the invention is formulated together with an orally acceptable carrier to provide oral compositions having a variety of forms such as referred to above. Depending on the form of the composition, the orally acceptable carrier can be a liquid carrier, a powder carrier, a dissolvable solid carrier, a gum base, a film forming polymer or polymers, and so on.

Various compositions of the invention contain an orally acceptable carrier and an antibacterial effective amount of compound (I). The effective amount is in the form of either a single compound or a mixture of compounds represented by structure (I). A mixture of compounds can result for example from intentional addition of separately synthesized compounds or from addition of a reaction product containing a mixture of substitution patterns of the groups $R^1$, $R^2$, $R^3$, and $R^4$.

As used herein, the "carrier" refers to components of the individual oral compositions in which the antibacterial compound or compounds of structure (I) are formulated as an active ingredient. In various embodiments, the carrier embraces all of the components of the oral composition except for the antibacterial compound (I). In other aspects, the term refers to components such as inactive ingredients, carriers, vehicles, and the like, that are commonly understood to persons of skill in the art to function as a carrier, filler or other relatively inert ingredient. In other words, the term carrier is used in different ways depending on context. Depending on the context, the oral compositions comprise other components in addition to the active compound (I) and the carrier. However, in all contexts, the components of the oral compositions of the invention can be divided into carrier components and the antibacterial compounds (I).

To illustrate in a non-limiting example for the case of toothpastes, the carrier can be said to be the water/humectant system that provides a large fraction by weight of the composition. Alternatively, the carrier component of a toothpaste composition may be considered as the water, humectant, and other functional components other than the antibacterial system. Whatever the context, the person of skill in the art recognizes that the toothpaste composition contains both antibacterial compounds (I) and an orally acceptable carrier for the compound.

To illustrate further, in a mouth rinse, the carrier is generally considered to be the water/alcohol liquid component in which the antibacterial compounds (I) are dissolved or dispersed. In a dissolvable lozenge, the carrier is generally understood to comprise the solid matrix material that dissolves slowly in the mouth to the oral surfaces in the mouth. In chewing gums, the carrier comprises a gum base, while in an edible strip, the carrier comprises one or more film forming polymers.

In all of the above examples, the oral composition, in whatever form, includes antibacterial compounds (I), a suitable carrier in an appropriate form, and other actives or functional materials needed to provide the oral compositions with desired properties. Additional active materials and functional materials are described below.

In addition to a biologically acceptable carrier, oral compositions of the invention contain an antibacterial effective amount of compound (I). In various embodiments, an antibacterial effective amount is from about 0.001% to about 10%, based on the total weight of the oral composition, for example from 0.01% to about 5% or about 0.1% to about 2%. The effective amount will vary depending on the form of the oral composition. For example, in toothpastes, tooth gels, and tooth powders, an effective amount is usually at least about 0.01% and more preferably at least about 0.05%. In some preferred embodiments, compound (I) is present in a toothpaste, gel, or powder at a level of 0.1% or more, to achieve a desired level of antibacterial activity. Normally, compound (I) is formulated at 5% or less, preferably about 2% or less, and more preferably about 1% or less. Concentrations in the upper end of these limits can be used, but are sometimes less preferred for economic reasons. In various embodiments, optimum effectiveness is achieved at from about 0.1% to about 1%, especially from about 0.1% to about 0.5% or about 0.1% to about 0.3%, wherein all percentages are based on the total weight of the oral composition. Amounts used in tooth gels, tooth powders, gums, edible strips, and the like are comparable to those used in toothpastes.

In mouth washes and rinses, an antibacterial effective amount of (I) is normally on the lower side of the above ranges. Typically, compound (I) is used at a level of about 0.001% (or 10 ppm) up to about 1% or less. Preferably, compound (I) is at about 0.5% or less or about 0.2% or less. Preferably it is about 0.01% (100 ppm) or greater. In various embodiments, compound (I) is present at from 0.03 to 0.12% by weight.

The statements herein for structure (I) also apply to structure (II), which illustrates an embodiment or species of structure (I) where $R^1$ and $R^2$ are both a hydrogen atom. In addition to the antibacterial compound (I), a number of active ingredients and functional materials are included in various compositions of the invention. Such materials include, without limitation, abrasives, humectants, surfactants, anticalculus agents, thickeners, viscosity modifiers, anticaries agents, flavorants, colorants, additional antibacterial agents, antioxidants, anti-inflammation components, and so on. They are added to the pastes, gels, rinses, gums, lozenges, strips, and other forms of the oral compositions of the invention according to known methods.

In various embodiments of the present invention, where the carrier of the oral care composition is solid or a paste, the oral composition preferably comprises a dentally acceptable abrasive material, which serves to either polish the tooth enamel or provide a whitening effect. Non-limiting examples include silica abrasives such as silica gels and precipitated silicas. Commercial embodiments include ZEODENT® 115, marketed by J. M. Huber and SYLODENT® XWA, SYLODENT® 783 or SYLODENT® 650 XWA of the Davison Chemical Division of W. R. Grace & Co. Other useful dentifrice abrasives include, without limitation, sodium metaphosphate, potassium metaphosphate, tricalcium phosphate, dihydrated dicalcium phosphate, aluminum silicate, calcined alumina, bentonite or other siliceous materials, or combinations thereof.

The abrasive is present in an effective amount. In embodiments where the oral composition is in a solid or paste form, the abrasive material is generally present at about 10% to about 99% of the oral composition. In certain embodiments, the polishing material is present in amounts ranging from about 10% to about 75% (for example about 10% to about 40% or about 15% to about 30%) in toothpaste, and from about 70% to about 99% in toothpowder.

In a still further embodiment a composition of the invention comprises at least one humectant, useful for example to prevent hardening of a toothpaste upon exposure to air. Any orally acceptable humectant can be used, including without limitation polyhydric alcohols such as glycerin, sorbitol, xylitol and low molecular weight PEGs. Most humectants also function as sweeteners. One or more humectants are optionally present in a total amount of about 1% to about 70%, for example about 1% to about 50%, about 2% to about 25%, or about 5% to about 15% by weight of the composition.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides, and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01% to about 10%, for example about 0.05% to about 5% or about 0.1% to about 2% by weight of the composition.

In another embodiment the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate (STPP), tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include polycarboxylate polymers. These include polymers or copolymers of monomers that contain carboxylic acid groups, such as acrylic acid, methacrylic acid, and maleic acid or anhydride. Non-limiting examples include polyvinyl methyl ether/maleic anhydride (PVME/MA) copolymers, such as those available under the GANTREZ® brand from ISP, Wayne, N.J., United States of America. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically about 0.01% to about 50%, for example about 0.05% to about 25% or about 0.1% to about 15% by weight.

In various embodiments, the anticalculus system comprises a mixture of sodium tripolyphsophate (STPP) and a tetrasodium pyrophosphate (TSPP). In various embodiments, the ratio of TSPP to STPP ranges from about 1:2 to about 1:4. In a preferred embodiment, the first anticalculus active ingredient, TSPP is present at about 1 to about 2.5% and the second anticalculus active ingredient, STPP is present at about 1 to about 10%.

In various embodiments, the anticalculus system further comprises a synthetic anionic polycarboxylate polymer. In one embodiment, the synthetic anionic polycarboxylate is present from about 0.1% to about 5%. In another embodiment, the synthetic anionic polycarboxylate is present from about 0.5% to about 1.5%, most preferably at about 1% of the oral care composition. In one embodiment according to the present invention, the anticalculus system comprises a copolymer of maleic anhydride and methyl vinyl ether, such as for example, the GANTREZ® S-97 product discussed above.

In various embodiments, the ratio of TSPP to STPP to the synthetic anionic polycarboxylate ranges from about 5:10:1 to about 5:20:10 (or 1:4:2). In one embodiment, the anticalculus system of the oral care composition comprises TSPP, STPP, and a polycarboxylate such as a copolymer of maleic anhydride and methyl vinyl ether at a ratio of about 1:7:1. In a non-limiting embodiment, the anticalculus system consists essentially of TSPP present at about 0.5% to about 2.5%, STPP present at about 1% to about 10%, and a copolymer of maleic anhydride and methyl vinyl ether present at about 0.5% to about 1.5%.

In a still further embodiment a composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

In a still further embodiment a composition of the invention comprises at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organo-modified clays, silica and the like. One or more viscosity modifiers are optionally present in a total amount of about 0.01% to about 10%, for example about 0.1% to about 5% by weight of the composition.

In another embodiment the composition comprises an orally acceptable source of fluoride ions. One or more such sources can be present. Suitable sources of fluoride ions include fluoride, monofluorophosphate and fluorosilicate salts, and amine fluorides, including olaflur (N'-octadecyltrimethylendiamine-N,N,N'-tris(2-ethanol)-dihydrofluoride). Any such salt that is orally acceptable can be used, including without limitation alkali metal (e.g., potassium, sodium), ammonium, stannous and indium salts and the like. Water-soluble fluoride-releasing salts are typically used. One or more fluoride-releasing salts are optionally present in an amount providing a total of about 100 to about 20,000 ppm, about 200 to about 5,000 ppm, or about 500 to about 2,500 ppm, fluoride ions. Where sodium fluoride is the sole fluoride-releasing salt present, illustratively an amount of about 0.01% to about 5%, about 0.05% to about 1% or about 0.1% to about 0.5%, sodium fluoride by weight can be present in the composition.

Other components include, without limitation, flavorants, colorants, and other active ingredients such as antioxidants and anti-inflammation agents. The components are formulated into oral compositions according to known procedures.

Toothpastes and gels contain major amounts of humectants and usually an abrasive compound or compounds for teeth cleaning. They are formulated with various active ingredients, such as anticaries agents, antiplaque compound, antiinflammation agents, and the like, in addition to the antibacterial compound (I).

Mouth rinses and mouth washes contain the active compound (I) in a liquid carrier such as water or water/ethanol. Generally, the compositions contain a major amount of solvent, up to 98 or 99% by weight. The active compound (I) is optionally formulated together with surfactants, colorants, flavorants, and other active ingredients.

The orally acceptable vehicle or carrier in a lozenge bead or tablet is a non-cariogenic, solid water-soluble polyhydric alcohol (polyol) such as mannitol, xylitol, sorbitol, malitol, hydrogenated starch hydrozylate, hydrogenated glucose, hydrogenated disaccharides, hydrogenated polysaccharides, and the like in an amount of about 85% to about 95% of the total composition. Emulsifiers such as glycerin, and tableting lubricants, in minor amounts of about 0.1% to 5%, may be incorporated into the tablet, bead or lozenge formulation to facilitate the preparation of the tablet beads and lozenges. Suitable lubricants include vegetable oils such as coconut oil, magnesium stearate, aluminum stearate, talc, starch and Carbowax. Suitable non-cariogenic gums include kappa carrageenan, carboxymethyl cellulose, hydroxyethyl cellulose and the like.

The lozenge, bead or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the antibacterial and anticalculus active ingredients of the present invention.

Chewing gum formulations typically contain a chewing gum base, one or more plasticizing agents, at least one sweetening agent and at least one flavoring agent, in addition to antibacterial compound (I). It is preferably a sugarless gum.

Gum base materials are well known in the art and include natural or synthetic gum bases thereof. Representative natural gums or elastomers include chicle, natural rubber, jelutong, balata, guttapercha, lechi caspi, sorva, guttakay, crown gum, and perillo, or mixtures thereof. Representative synthetic gums or elastomers include butadiene-styrene copolymers, polyisobutylene and isobutylene-isoprene copolymers. The gum base is incorporated in the chewing gum product at a concentration of about 10% to about 40% and preferably about 20% to about 35%.

Plasticizing/softening agents include without limitation gelatin, waxes and mixtures thereof in amounts of about 0.1% to about 5%. The sweetening agent ingredient used in the practice of this invention may be selected from a wide range of materials, and include the same artificial and polyol sweeteners used for the preparation of tablets, beads and lozenges. Polyol sweeteners such as sorbitol and malitol are present in the chewing gum composition of the present invention in amounts of about 40% to about 80% and preferably about 50% to about 75%. In a non-limiting embodiment, an artificial sweetener is present in the chewing gum composition of the present invention in amounts of about 0.1% to about 2% and preferably about 0.3% to about 1%.

The invention has been described above with respect to various preferred embodiments, Further non-limiting description is provided in the following examples.

EXAMPLES

Example 1

Synthesis of 3',5-dibutyl-2,4'-dimethoxy-1,1'-biphenyl and 3',5-dibutyl-2,4'-dihydroxy-1,1'-biphenyl At 120° C., p-iodoanisole is reacted with 2-methoxyphenylboronic acid in the presence of palladium tetraphenyl phosphate, potassium carbonate and the phase transfer catalyst, tetrabutyl ammonium bromide to yield 2,4'-dimethoxybiphenyl (66%), which is then brominated at 0° C. in ethylene dichloride to produce 5,5'-dibromo-2,4'-dimethoxybiphenyl in 80% yield. n-butyl bromide is reacted with the dibromo intermediate in the presence of magnesium and cuprous iodide at −10° C. to produce in 50% yield 3',5-dibutyl-2,4'-dimethoxy-1,1'-biphenyl. Demethylation with boron tribromide gives 3',5-dibutyl-2,4'-dihydroxy-1,1'-biphenyl (17% yield).

What is claimed is:

1. An antiplaque oral composition comprising
an orally acceptable carrier; and
an antibacterial effective amount of a compound of structure (I)

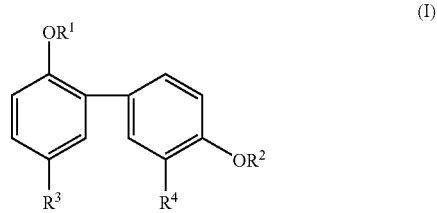

wherein $R^1$ and $R^2$ are independently a hydrogen atom or a lower $C_{1-4}$ alkyl group and $R^3$ and $R^4$ are independently an alkenyl or alkyl group having from 1 to 20 carbon atoms, with the proviso that $R^3$ and $R^4$ are not both 2-propenyl or n-propyl when $R^1$ and $R^2$ are both hydrogen atoms.

2. The composition according to claim 1, comprising 0.001% to 10% by weight (I).

3. The composition according to claim 1, wherein the carrier is a liquid carrier.

4. The composition according to claim 1, wherein the carrier is a powder carrier.

5. The composition according to claim 1, wherein the carrier dissolves upon contact with an oral environment.

6. The composition according to claim 1, wherein the composition is in a form selected from a toothpaste, a gel, a mouthrinse, a toothpowder, a lozenge, a chewable pellet, a gum, and an edible strip.

7. The composition according to claim 1, wherein $R^1$ and $R^2$ are a hydrogen atom.

8. The composition according to claim 1, wherein $R^3$ and $R^4$ are an alkyl group.

9. The composition according to claim 1, wherein $R^3$ and $R^4$ independently have 1 to 8 carbon atoms.

10. The composition according to claim 1, wherein $R^3$ and $R^4$ independently have 4 to 8 carbon atoms.

11. A toothpaste or gel composition comprising
at least one humectant;
at least one abrasive compound; andan antibacterial effective amount of a compound of structure (I):

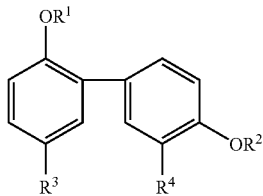

wherein $R^1$ and $R^2$ are independently a hydrogen atom or a lower $C_{1-4}$ alkyl group and $R^3$ and $R^4$ are independently an alkenyl or alkyl group having from 1 to 20 carbon atoms, with the proviso that $R^3$ and $R^4$ are not both 2-propenyl or n-propyl when $R^1$ and $R^2$ are both hydrogen atoms.

12. The composition according to claim 11, further comprising an antitartar effective amount of an anticalculus agent comprising at least one phosphate compound.

13. The composition according to claim 11, wherein the anticalculus agent comprises tetrasodium pyrophosphate and trisodium polyphosphate.

14. The composition according to claim 12, wherein the anticalculus agent comprises a synthetic anionic polycarboxylate.

15. The composition according to claim 14, wherein the synthetic anionic polycarboxylate comprises a maleic anhydride copolymer with methyl vinyl ether.

16. The composition according to claim 11, comprising:
0.01-5% by weight of a compound of structure (I):

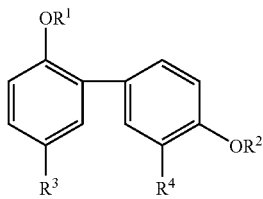

1-70% by weight or at least one humectant;
1-70% by weight of at least one abrasive compound;
0.5-2.5% by weight of tetrasodium pyrophosphate (TSPP); and
1-10% by weight of sodium tripolyphosphates (STPP).

17. The composition according to claim 16, wherein the weight radio of TSPP:STPP is about 1:7.

18. The composition according to claim 16, further comprising an anionic polycarboxylate.

19. The composition according to claim 18, wherein the ratio of TSPP:STPP:polycarboxylate is about 1:7:1.

20. A method for inhibiting bacterial growth in the oral cavity of an animal, comprising applying to the oral surfaces of the subject animal an antibacterial composition comprising a compound of structure (I)

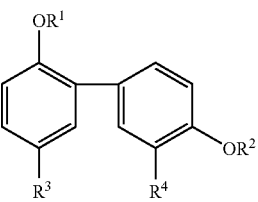

wherein $R^1$ and $R^2$ are independently a hydrogen atom or a lower $C_{1-4}$ alkyl group and $R^3$ and $R^4$ are independently an alkenyl or alkyl group having from 1 to 20 carbon atoms, with the proviso that $R^3$ and $R^4$ are not both 2-propenyl or n-propyl when $R^1$ and $R^2$ are both hydrogen atoms.

21. The method according to claim 20, wherein the application comprises brushing the teeth.

22. The method according to claim 20, wherein the application comprises rinsing the oral surfaces with a mouth rinse composition comprising (I).

23. The method according to claim 20, wherein the antibacterial composition is a toothpaste or gel.

24. The method according to claim 20, wherein the antibacterial composition is a mouth rinse.

25. The method according to claim 20, wherein the animal is selected from mammals, equine species, canine species, feline species and humans.

* * * * *